(12) United States Patent
Dubé et al.

(10) Patent No.: US 7,276,127 B2
(45) Date of Patent: Oct. 2, 2007

(54) METHOD AND APPARATUS FOR CLEANING WITH INTERNALLY REFLECTED ELECTROMAGNETIC RADIATION

(75) Inventors: George Dubé, Chesterfield, MO (US); Samuel W. Bross, Palmyra, MO (US)

(73) Assignee: Metastable Instruments, Inc., St. Charles, MO (US)

( * ) Notice: Subject to any disclaimer, the term of this patent is extended or adjusted under 35 U.S.C. 154(b) by 490 days.

(21) Appl. No.: 10/351,839

(22) Filed: Jan. 27, 2003

(65) Prior Publication Data

US 2003/0147159 A1  Aug. 7, 2003

Related U.S. Application Data

(60) Provisional application No. 60/353,109, filed on Feb. 1, 2002.

(51) Int. Cl.
*B08B 7/00* (2006.01)

(52) U.S. Cl. .................. 134/1; 134/1.3; 356/237.2; 250/341.8

(58) Field of Classification Search ............ 134/1, 134/1.3; 356/237.2; 250/341.8
See application file for complete search history.

(56) References Cited

U.S. PATENT DOCUMENTS

| | | | |
|---|---|---|---|
| 4,292,093 A | 9/1981 | Ownby et al. | |
| 4,718,974 A | 1/1988 | Minaee | |
| 4,720,621 A | 1/1988 | Langen | |
| 4,980,536 A | 12/1990 | Asch et al. | |
| 4,987,286 A | 1/1991 | Allen | |
| 5,024,968 A | 6/1991 | Engelsberg et al. | |
| 5,099,557 A | 3/1992 | Engelsberg et al. | |
| 5,151,134 A | 9/1992 | Boquillon et al. | |
| 5,344,493 A | 9/1994 | Jackson | |
| 5,439,642 A * | 8/1995 | Hagmann et al. | ............. 422/22 |
| 5,531,857 A | 7/1996 | Engelsberg et al. | |
| 5,643,472 A | 7/1997 | Engelsberg et al. | |

(Continued)

FOREIGN PATENT DOCUMENTS

WO    WO91/03393    * 3/1991

OTHER PUBLICATIONS

Francis A. Jenkins and Harvey E. White, Physical Optics, Fundamentals of Optics, 3rd Ed., Chapter 25, 1957.

J.D. Kelley, Particle removal from surfaces by pulsed laser irradiation SPIE vol. 1524 1991.153.

Y.F. Lu et al., Recent Progress on the Modeling of Laser Surface Cleaning, vol. 6, 2000.

Xiulan Huai et al., Heat and Mass Transfer Analysis in Laser Drying, Jun. 1-12, 2001.

(Continued)

*Primary Examiner*—M. Kornakov
(74) *Attorney, Agent, or Firm*—Gallop, Johnson & Neuman, LC

(57) ABSTRACT

A method and apparatus for cleaning, detecting, and/or removing contamination from the surfaces of nominally transparent materials utilizing internal illumination of those surfaces with at least one electromagnetic radiation beam at an angle of incidence equal to or greater than the critical angle for total internal reflection. With appropriate selection of light sources and materials, the technique is effective at detecting and removing water, ice, particles, films and a variety of contaminants.

33 Claims, 8 Drawing Sheets

U.S. PATENT DOCUMENTS

| | | |
|---|---|---|
| 5,669,979 A | 9/1997 | Elliott et al. |
| 5,800,625 A | 9/1998 | Engelsberg et al. |
| 5,808,734 A * | 9/1998 | Kolari ............... 356/237.2 |
| 5,821,175 A | 10/1998 | Engelsberg et al. |
| 5,948,172 A | 9/1999 | Neiheisel |
| 5,958,268 A | 9/1999 | Engelsberg et al. |
| 6,420,076 B1 | 7/2002 | Fukumoto |
| 6,494,217 B2 | 12/2002 | Thompson et al. |
| 2002/0023902 A1 | 2/2002 | Allen |
| 2002/0029956 A1 | 3/2002 | Allen |
| 2002/0105997 A1 | 8/2002 | Zhang |

OTHER PUBLICATIONS

M.D. Crisp et al., Applied Physics Letters Oct. 15, 1972, vol. 21, No. 8 pp. 364-366.

Arenberg et al., SPIE vol. 4347 (2001) Calculation of relative damage thresholds . . . reflection surface.

Warren, Applied Optics vol. 23, No. 8 Apr. 15, 1984 Optical constants . . . ultraviolet to microwave.

Chandler et al., Applied Optics vol. 22, No. 24, Dec. 15, 1983 Attenuated . . . constants of powders.

Brown, High-Peak Power Nd:Glass Laser Systems 1981 pp. 128-145.

* cited by examiner

METHOD AND APPARATUS FOR CLEANING WITH INTERNALLY REFLECTED ELECTROMAGNETIC RADIATION

FIELD OF THE INVENTION

The present invention relates to a method and an apparatus for cleaning, detecting, and/or preventing contamination on a surface by internal illumination of the surface with electromagnetic radiation at an angle of incidence greater than or equal to the critical angle for total internal reflection.

BACKGROUND OF THE INVENTION

There are many situations where it is desired to remove, reduce the amount of, or prevent the formation of contaminants such as water, ice, particulate, and other substances from windows or other surfaces. Recent solicitations have sought improved ways to keep submarine periscope windows dry and clean, ways to keep clean the mirrors and windows of high power lasers, and ways to clean the surfaces of the "last optic" in future laser fusion reactors. Photographs and TV pictures are also sometimes seriously degraded by the water drops on the protective window in front of the camera. Forward looking infrared (FLIR) systems also benefit from clean and dry windows. In addition, the push to high yields of smaller and smaller circuit features in the semiconductor industry has made contamination removal from semiconductor surfaces a high priority.

A great deal of research and development has been published on the use of lasers to remove contaminants, such as particles and films, from the surfaces of solid materials. All of this prior work illuminated the contaminated surface from the outside of the surface, usually from the side that is exposed to vacuum or air.

SUMMARY OF THE INVENTION

The present invention provides a method and apparatus for cleaning, detecting and/or removing contamination from a surface of a material by internally reflecting electromagnetic radiation within the material at angles of incidence equal to or greater than the critical angle for total internal reflection. The present invention may also be used to reduce the accumulation of contaminants on the surface. The method and apparatus is helpful in both detecting and removing contaminants from the surfaces of windows, mirrors, view ports, lenses, semiconductor materials, etc. without having to disrupt the external observation of the surface being cleaned. Thus, there are many markets and uses for the present invention in detecting and/or removing contaminants from the surface of semiconductors and optical elements such as windows, view ports, lenses, semiconductor materials and mirrors.

In general, the surface to be inspected and/or cleaned should be a smooth surface of a material that is transparent to the electromagnetic radiation chosen for the inspecting/cleansing task(s). As used herein, transparent shall mean transparent to the inspecting/cleansing electromagnetic radiation and not necessarily to visible light.

In a particularly preferred embodiment of the present invention, 2.94 µm erbium laser light may be used to remove water, ice, particles and other contaminants from a surface.

One aspect of the present invention is to provide for detecting the presence of contaminants upon the surface of a nominally transparent material.

Another aspect of the present invention is to remove contaminants from the surface of a nominally transparent material.

Another aspect of the present invention is to reduce the amount of contaminants from the surface of a nominally transparent material.

Another aspect of the present invention is to reduce the likelihood that contaminants will be deposited upon the surface of a nominally transparent material.

Another aspect of the present invention is to improve the efficiency of laser or photo cleaning on nominally transparent materials by recycling the light via total internal reflections.

Another aspect of the present invention is to provide a laser or photo cleaning procedure that treats both surfaces of windows and similar optical elements in the same manner.

Another aspect of the present invention is to provide a cleaning process that requires no fluids or consumables and leaves no hazardous waste.

Another aspect of the present invention is to provide a cleaning process that does not significantly increase the infrared signature of the object being cleaned.

Another aspect of the present invention is to provide a cleaning process that may be qualified for use in space.

Another aspect of the present invention is to provide an efficient deicing process.

Another aspect of the present invention is to allow a cleaning process that is compatible with any transparent coating, such as anti-reflective coatings or abrasion resistant coatings.

These and other aspects are achieved herein by the present invention.

DETAILED DESCRIPTION OF PREFERRED EMBODIMENTS

The present invention provides a method and apparatus for cleaning, detecting and/or removing contamination from a surface of a material by internally reflecting electromagnetic radiation within the material at angles of incidence equal to or greater than the critical angle for total internal reflection so as to remove a contaminant from the surface. The present invention may also be used to reduce and prevent the accumulation of contaminants on the surface. Electromagnetic radiation includes energy across the x-ray, ultraviolet, visible light and infrared spectrum, from a variety of sources, such as, for example, lasers, lamps, etc. Visible light or light, as used herein, is a type of electromagnetic radiation. As used herein, a light beam is electromagnetic radiation of limited transverse extent.

Figure 1:
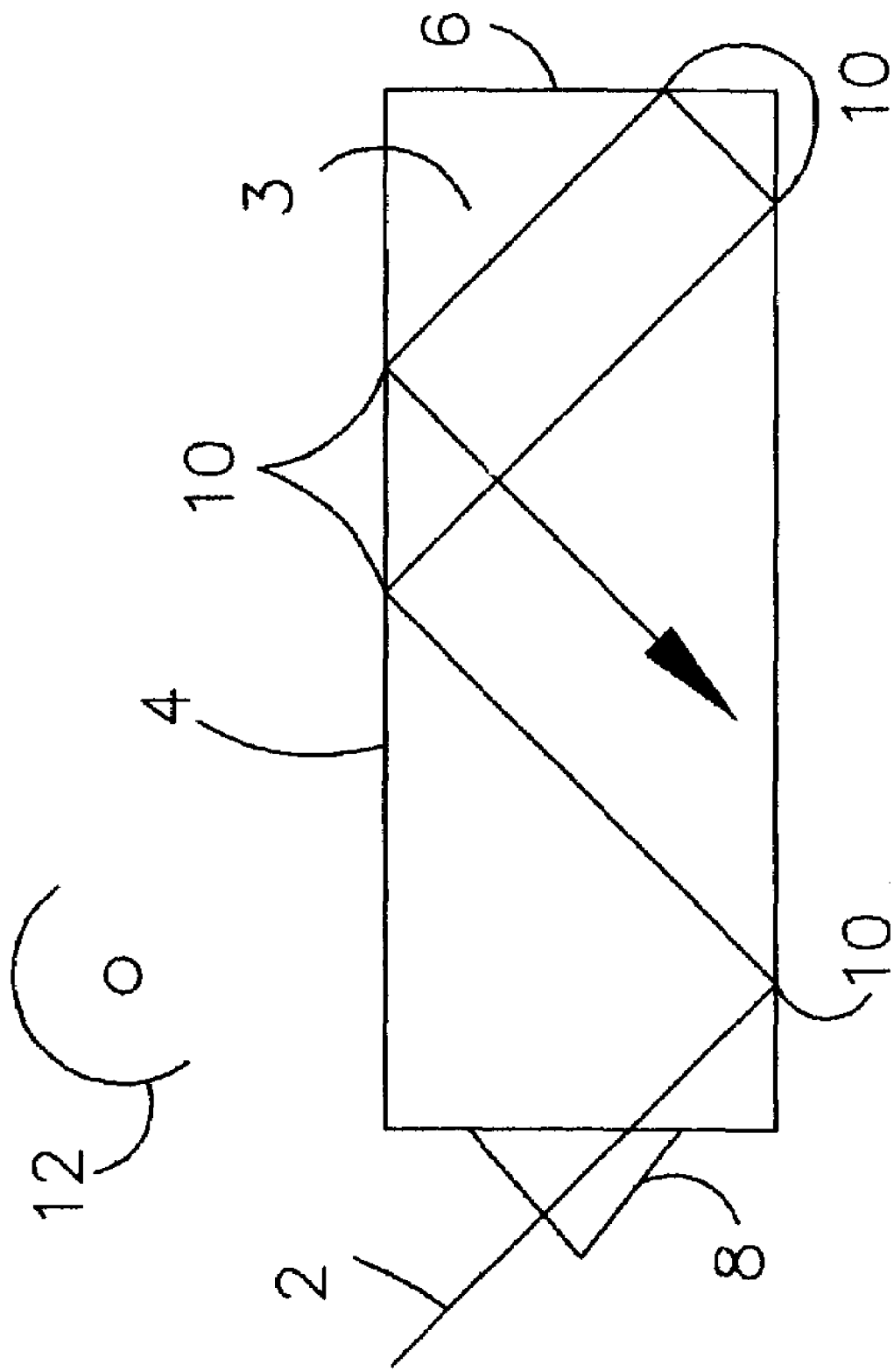
FIG. 1 shows an example of light undergoing attenuated total internal reflection after entering a substrate for the purpose of cleaning the surfaces of the substrate.

As shown in FIG. 1, the method and apparatus of the present invention illuminates a surface 4 from the inside of a substrate or a material 3, so that internally reflecting electromagnetic energy 2, from a laser beam or other source, will be coupled into, i.e., absorbed by, any contaminants on the surface 4 of the substrate or the material 3 via attenuated total internal reflection (ATIR) and/or total internal reflection (TIR) altered by the presence of the contaminant on the surface 4. A coupling device 8 may be used to direct the electromagnetic energy 2 into the substrate or the material 3. The internal reflection of the electromagnetic energy 2 is shown at points 10. Absorbing contaminants on the surface 4 of the substrate or the material 3 will absorb the electromagnetic energy so as to remove the contaminant from the surface 4 via the (ATIR). Nonabsorbing contaminants may be removed by gradients of the electromagnetic field caused by the presence of the contaminant. A photodetector 12 may be included to detect any light that leaks out of the substrate or the material 3 due to altered total internal reflection.

Besides the convenience of ATIR, the electric field of light waves is often higher at the surface for internal reflection than it is for transmission or external reflection. This enhanced electric field for internal reflection increases the effectiveness of light at removing contaminants. In extreme cases, such as water or ice upon a low index substrate (such as calcium fluoride) the ATIR may actually turn into external reflection (the complex refractive index of the contaminant is no longer lower than that of the substrate). This too will couple a large fraction of the laser power into the contaminant, as desired. When the contamination is removed, the light will return to experiencing total internal reflection.

A brief discussion of the various conditions encountered when light encounters an interface between materials, and/or within a material, including internal reflection, will now follow, also including a discussion of total internal reflection, frustrated, altered, and attenuated total internal reflection.

Figure 2:
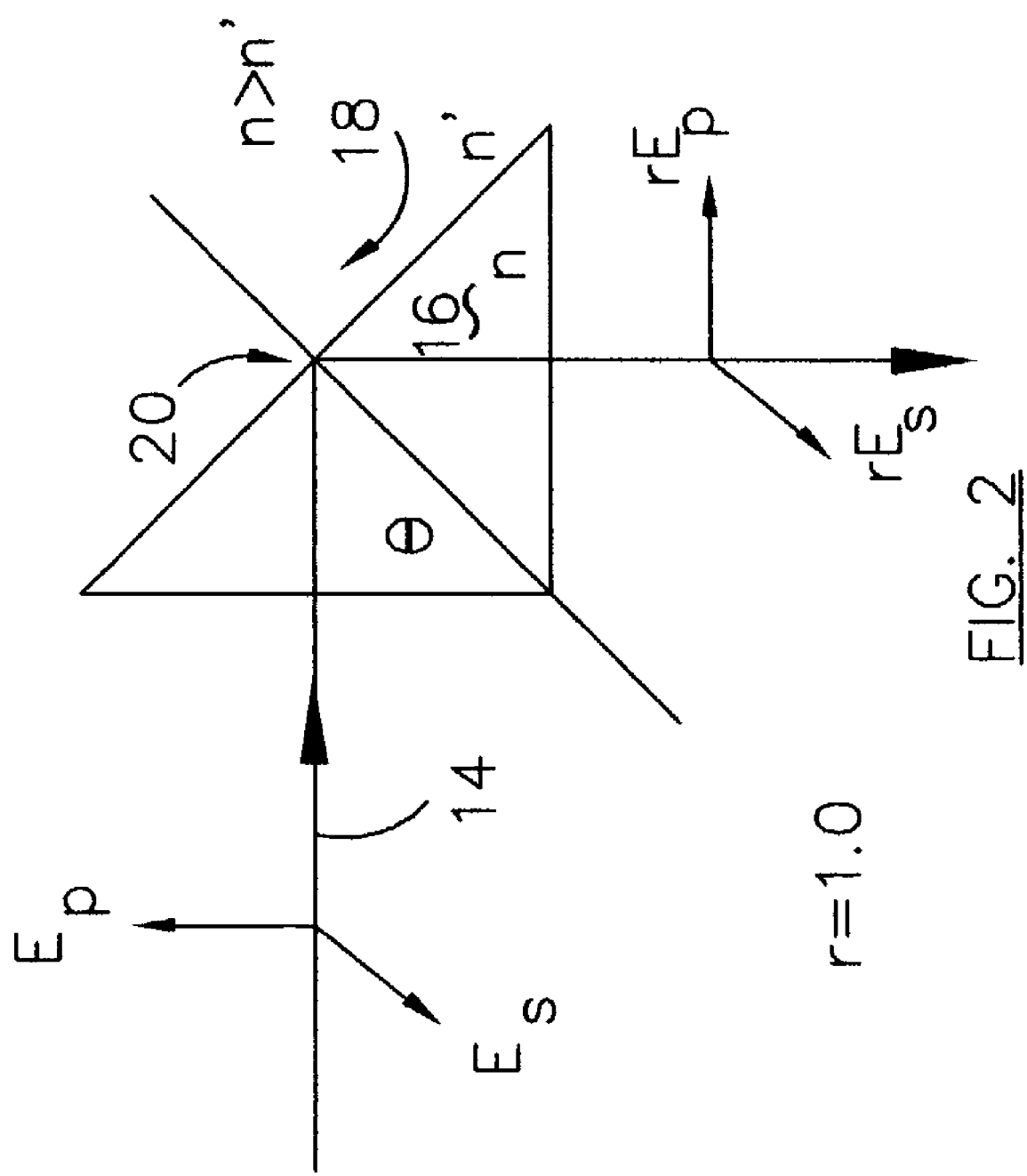
FIG. 2 shows an example of light undergoing total internal reflection at the interface of two nonabsorbing materials.

When light encounters an interface between two transparent materials with different indices of refraction (n and n'), some light is generally reflected. If the light originates from the material with the lower refractive index (often air), the reflection is called "external" reflection. As shown in FIG. 2, when a light 14 strikes an interface from the high refractive index side, that light 14 is said to undergo "internal" reflection. In FIG. 2, a first transparent material 16 has a higher refractive index n than the refractive index n' of a second transparent material 18 and the light 14 undergoes total internal reflection at interface 20.

Total (100%) internal reflection (TIR) will occur whenever the sine of the angle of refraction (θ'), as given by Snell's Law (Eq. 1), is greater than or equal to one.

$$\sin \theta' = \{n/n'\}\sin \theta \geq 1 \qquad \text{Eq. 1}$$

where θ is the angle of incidence and n>n'. "θ'" is not shown in FIG. 2 because there is no refracted beam with TIR. $E_s$ and $E_p$ are the linearly polarized components of the electric vector, "r" is the reflection coefficient of the electric field. The reflectivity of the light is $R=r^2$. The smallest angle (θ) that results in TIR is called the "critical angle for total internal reflection" or simply the "critical angle" ($\theta_c$).

As the angle of incidence increases, the ratio of refractive indices (n/n') required for total internal reflection decreases. Thus, for example, in optical fibers or planar waveguides, where the angle of incidence is just under 90 degrees, a refractive index difference of only a fraction of one percent will support TIR. TIR is supported in macroscopic structures such as windows and laser mirrors at modest angles of incidence, if the ratio of refractive indices is large. Many common semiconductor materials have a large (>2.0) refractive index, which makes them particularly well suited for the total internal reflection of light within them.

As shown in FIG. 2, the light 14 penetrates into the second transparent material 18 for a distance that is generally less than one wavelength of the light 14, but this is an evanescent wave, which does not transport any power into the second transparent material 18. In the steady state the TIR reflectivity is truly 100%.

Figure 3:
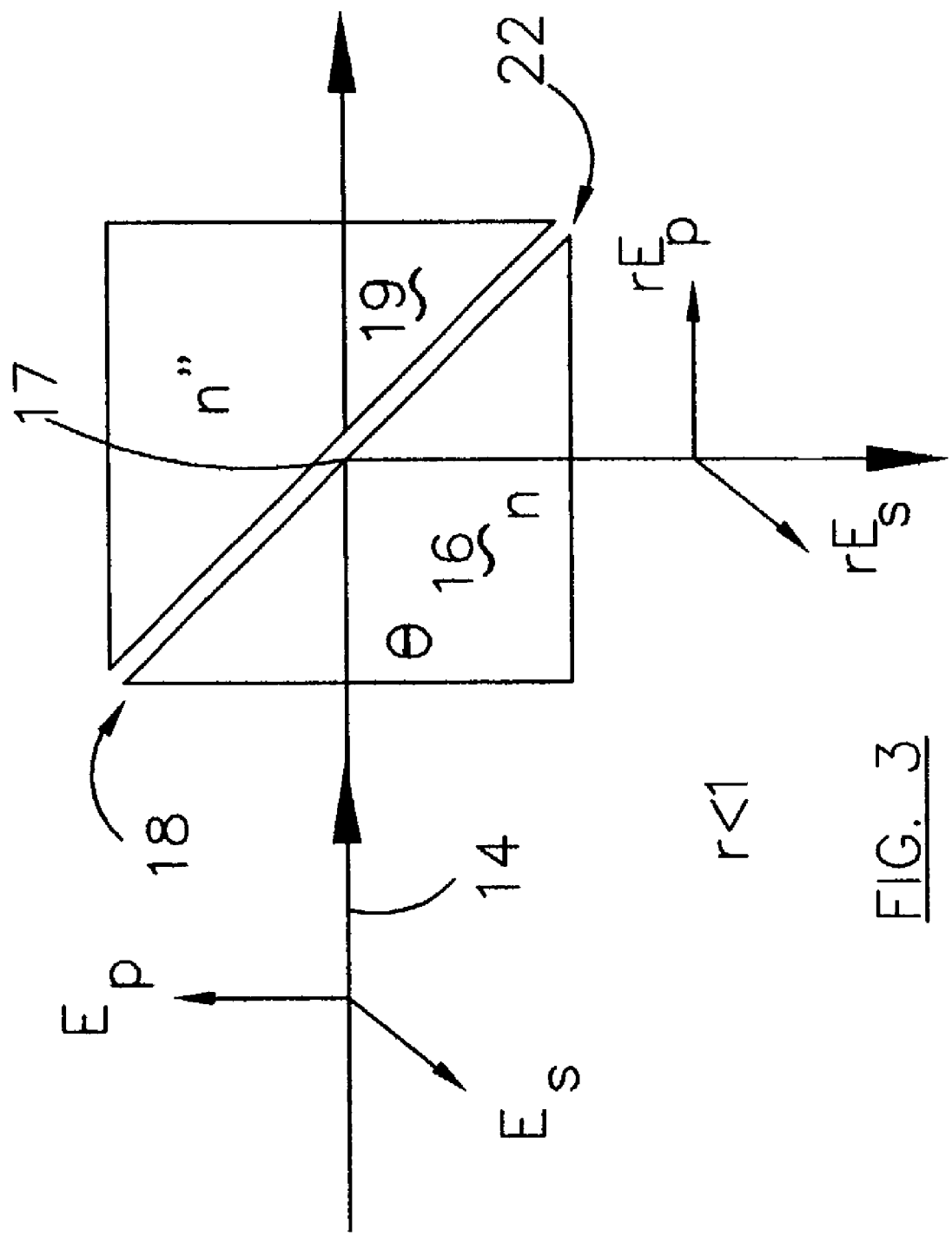
FIG. 3 shows an example of light undergoing frustrated total internal reflection.

If a third transparent material 19 with refractive index n" is placed very close to the first transparent material 16, as shown in FIG. 3, the TIR may be "frustrated" by the third transparent material 19. In the case of frustrated total internal reflection, the reflection at a first interface 17 drops below 100%, and light is coupled across a thin gap 22 and into the third transparent material 19. In frustrated total internal reflection, no light is absorbed; all light is either reflected or transmitted.

Figure 4:
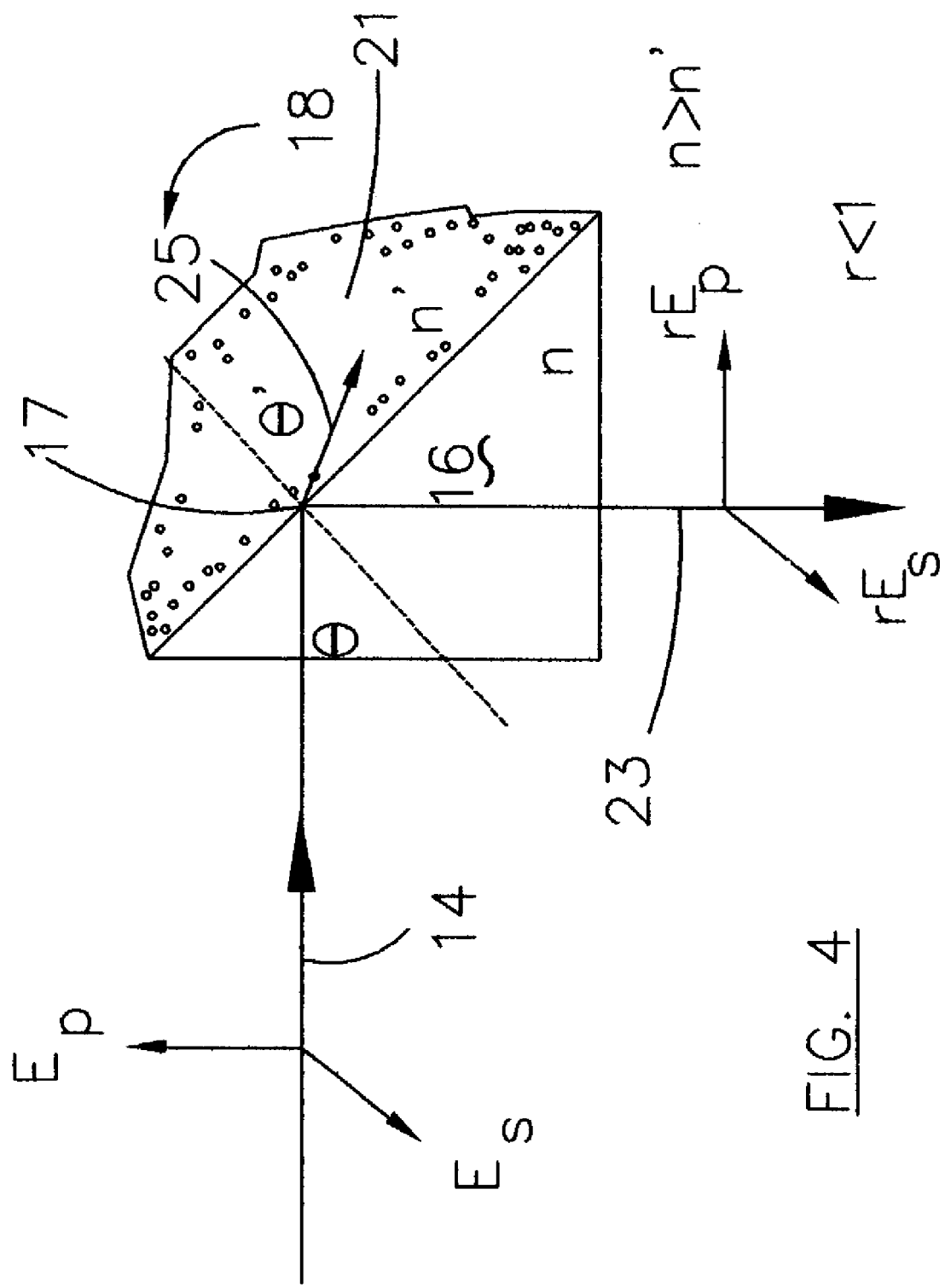
FIG. 4 shows an example of attenuated total internal reflection at an interface of nonabsorbing and absorbing materials.

Finally, as shown in FIG. 4, the case where a second (lower index) material is absorbing (not transparent) is considered. The refractive index of transparent materials is real. The refractive index (n') of absorbing materials is complex, with the imaginary part of the index (n'k') indicating the strength of the absorption.

$$n' = n'(1+ik') \qquad \text{Eq. 2}$$

The commonly used "absorption coefficient" (X), which is the reciprocal of the "absorption depth" is given by, $$X' = 4\pi n'k'/\lambda \qquad \text{Eq. 3}$$

where λ is the vacuum wavelength of the light.

If, as shown in FIG. 4, an absorbing material 21 (not transparent) is to the right of the first interface 17, the total internal reflection of the light 14 normal to the interface will be "attenuated". Under these conditions, an attenuated total internal reflection (ATIR) 23 of the light 14 will be less than 100% of the light 14 and power 25 will be transmitted (coupled) into (absorbed by) the absorbing material 21.

The amount of incident light reflected (either externally or internally) can be calculated from the Fresnel Reflection Formulae, if the angle of incidence (θ), polarization ("s" or "p") of the light and refractive indices (n and n') are known. In the case of complex refractive indices (absorbing materials), these formulae become rather complicated, but they are handled by modern computer programs, such as those used to design optical thin films. "Simplified" versions of these formulae as shown below for the case we are considering (transparent substrate coated by an absorbing layer), have been developed, $$R_s = 1 - 4a\cos\theta/\{a^2 + G + (a + \cos\theta)^2\} \qquad \text{Eq. 4}$$

where, $$a = \{[G^2 + 4k'^2N^4]^{1/2} - G]/2\}^{1/2}$$

$$G = \sin^2\theta - N^2(1 - k'^2) \qquad N = n'/n$$

$$R_p = R_s\{1 - 4a\sin\theta\tan\theta/[a^2 + G + (a + \sin\theta\tan\theta)^2]\}. \qquad \text{Eq. 5}$$

Controlling the polarization of the internally reflected light gives us another variable for adjusting the absorption to optimize contamination removal.

As used herein, the term "altered total internal reflection" refers to any reduction of the total internal reflection of electromagnetic radiation.

The present invention will now be discussed with reference to the types of contaminants and their removal, preferred embodiments, and preferred operating conditions.

Many different contaminants may be removed by the methods and apparatus of the present invention. Water and ice are well suited for removal by ATIR applications. They feature strong absorption (k'~0.28) near 2.94 µm in the mid infrared (MIR), resulting in a penetration depth or absorption depth of less than one micrometer. Erbium lasers, which lase at 2.94 µm, are especially effective at heating and removing water from surfaces via ATIR.

In the field of laser cleaning, contaminants are generally classified into the following groups: particles that absorb laser light, particles that do not absorb laser light, thin films, smears or deposits of oils, greases, condensed vapors, and frozen liquids/vapors.

Particles that absorb the laser light include metallic particles and some nonmetallic particles. The nonmetallic particles may be organic or inorganic. Illuminating such a particle with a short pulse of laser light causes the particle to be heated, to expand suddenly, and thus be accelerated off of the surface.

Particles that do not absorb laser light include inorganic substances, often composed of fine particles of glass, silica and/or alumina. These particles may be removed by short pulses of light that are absorbed by a fluid that is already present, as with capillary condensation, or added for that purpose. Capillary condensation is thought to be one of the stronger forces holding very small particles to smooth semiconductor surfaces.

Thin films, smears or deposits of oils, greases, condensed vapors, and frozen liquids/vapors may also be removed.

Other cleaning techniques may be used in conjunction with the methods and apparatus of the present invention. In some cases, a gas is blown across the surface to sweep away particles dislodged by the laser to prevent them from being redeposited on the surface.

For absorbing contaminants on a transparent substrate, the sudden heating and expansion of the contaminant (from the laser) removes the contaminant by thermal expansion/shock and/or vaporization and/or forces from steep electric field gradients. For nonabsorbing particle contaminants, an absorbing film is sometimes added to the surface so that sudden expansion/movement of the film (from the laser) dislodges the particles embedded in the film.

Figure 5:
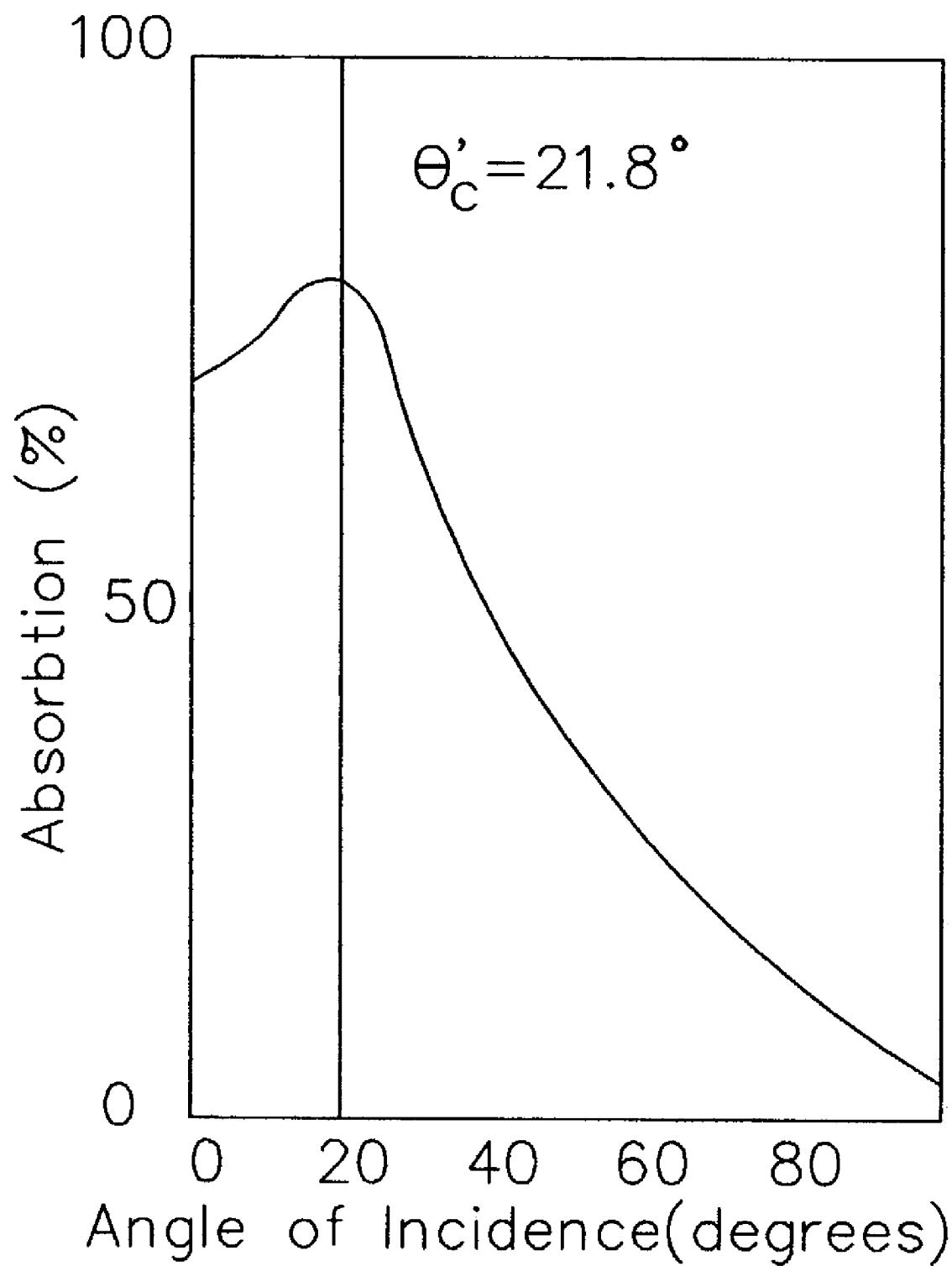
FIG. 5 shows an example of the absorption from attenuated total internal reflection for water on germanium at a wavelength of 2.94 µm.

There is clear theoretical and experimental evidence that a large fraction of light can be coupled from a transparent substrate into an absorbing contaminant on the surface of that substrate via attenuated total internal reflection. The purpose of this invention is to optimize this phenomenon for the decontamination of surfaces. For example, in the case of a layer of water (k'~0.28) on a germanium substrate, near the critical angle, more than 80% of the light is absorbed (FIG. 5). If the angle of incidence increases by 30 degrees, the absorption upon each reflection is still more than 20%.

Approximately 1 J/cm$^2$ is required to vaporize a thin (<5 µm) layer of water from the surface of a substrate. Such irradiance is readily available from existing lasers known to one of ordinary skill in the art. The present inventors have demonstrated the removal of water from the surface of a transparent material via attenuated total internal reflection of pulsed 2.94 µm light by both vaporizing the water and by explosive blow-off of the water.

A 2.94 µm laser, or similar mid-infrared light source, heats a very thin layer of ice directly in contact with the substrate, so it is not necessary to melt all the way through the ice. By breaking the adhesion of the ice to the substrate, gravity, normal vibrations and aerodynamic forces may easily remove the bulk of the ice. As the volume of ice being melted is extremely small, very little power is required.

The present invention provides many practical advantages. Unlike conventional heating, the proposed technique should not significantly increase the IR signature of any platform using it. This is of concern for military vehicles that do not wish to generate heat or infrared light as it may allow their detection by hostile forces. The only time the 2.94 µm light leaves the optical element is when a contaminant is being illuminated. Even if this light leaves the platform, it will not travel far before it is absorbed by the moisture in the air.

Figure 6A:
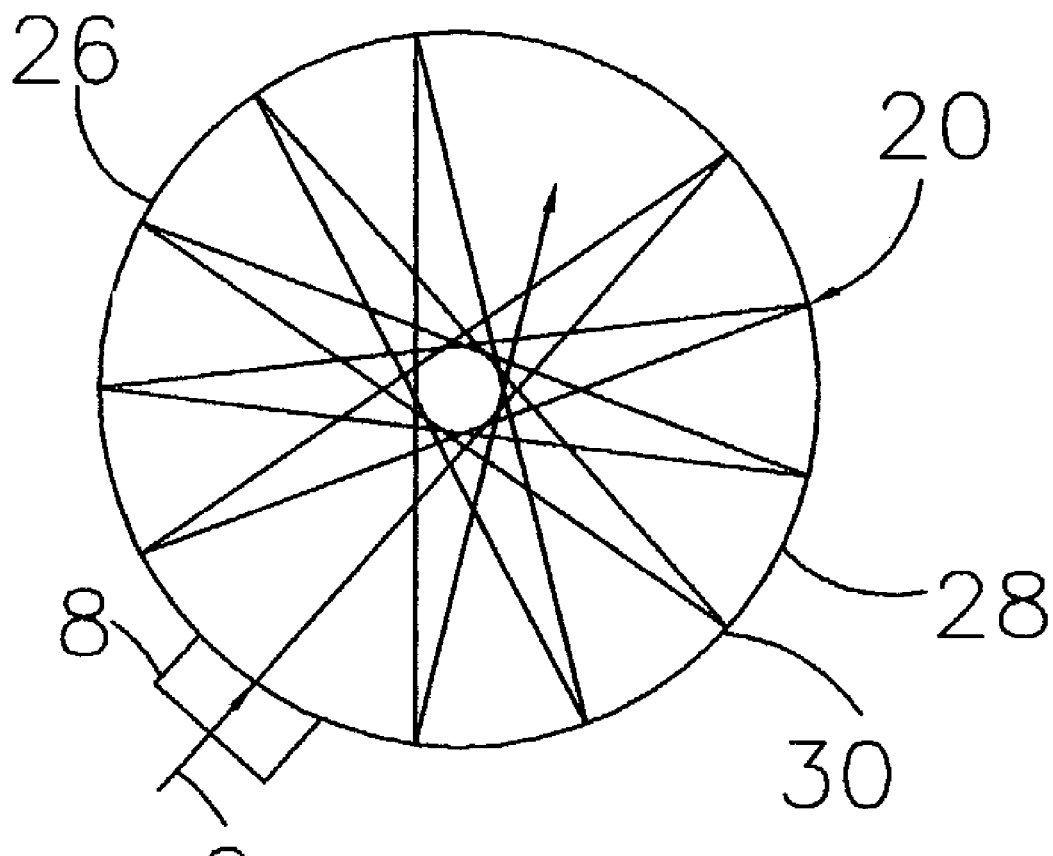
FIGS. 6(a) and 6(b) show examples of parasitic oscillations in a high index substrate.
Figure 6B:
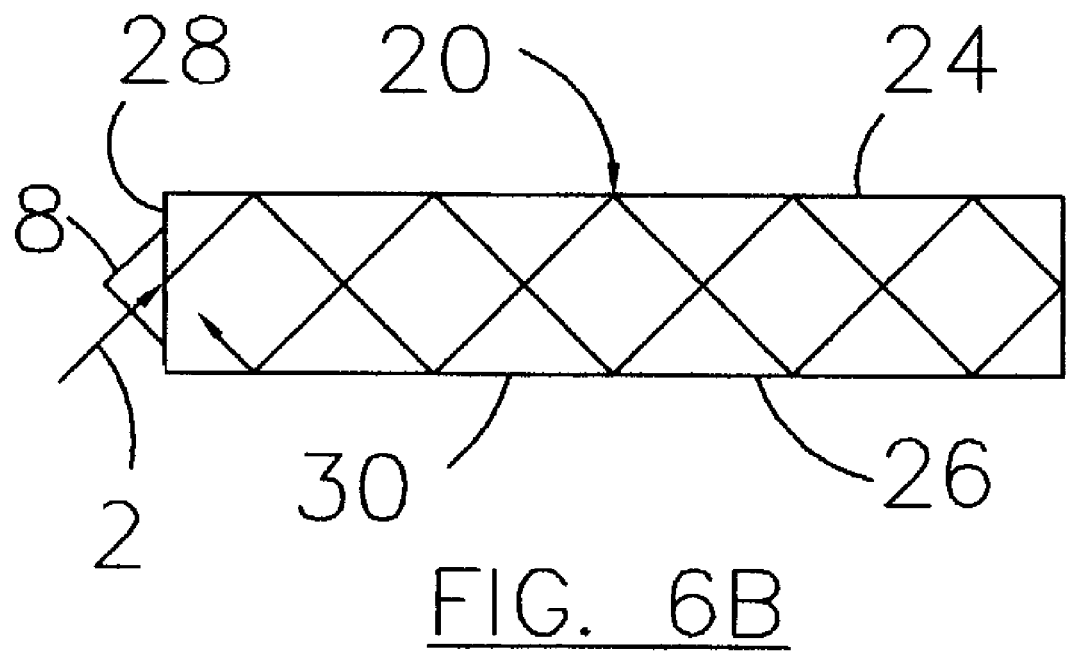
Figure 7A:
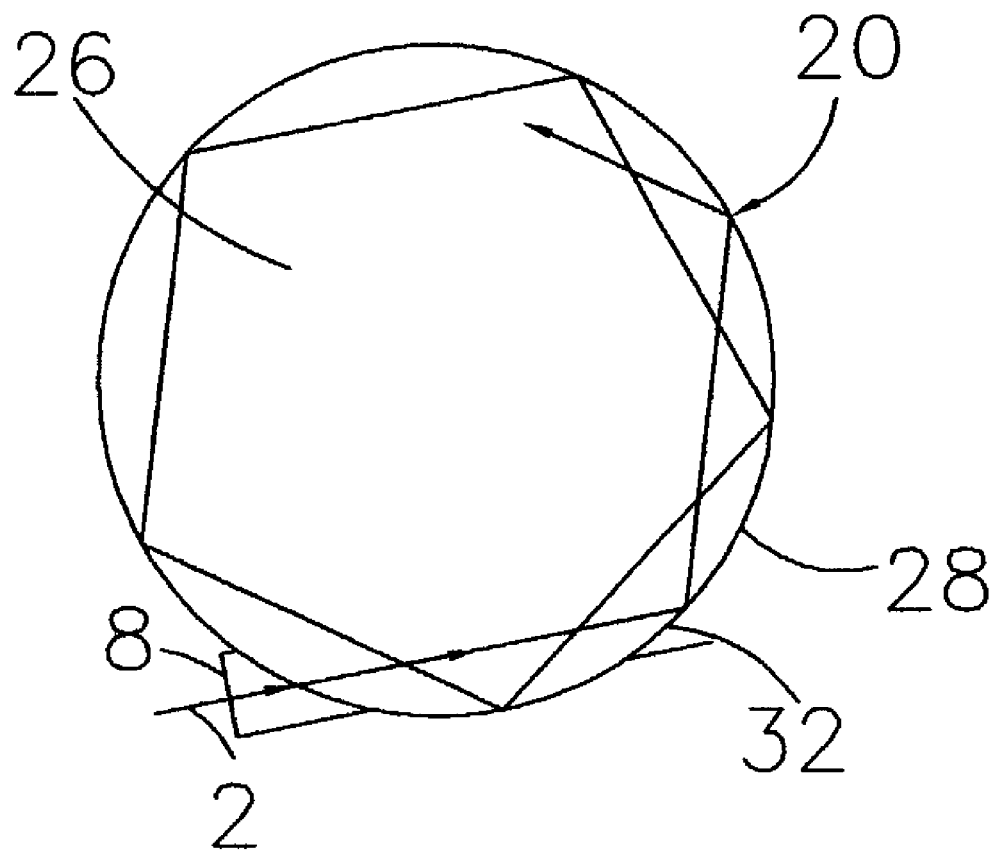
FIGS. 7(a) and 7(b) show examples of parasitic oscillations in a low index substrate.
Figure 7B:
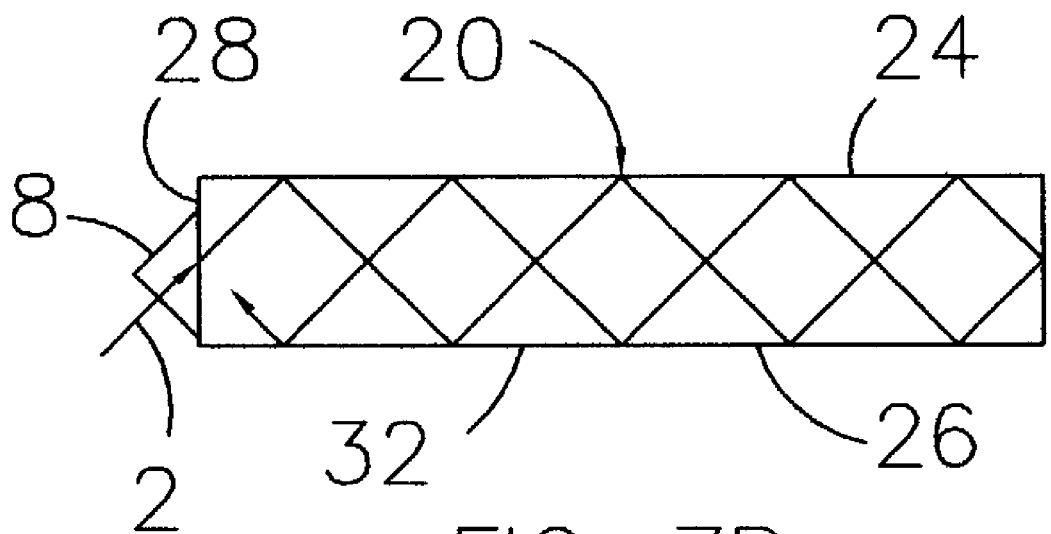

One consequence of total internal reflection is "parasitic oscillations" (FIGS. 6(a) and 6(b)). A parasitic oscillation is a ray path that stays within the material because at every encounter with a surface 24, the light 2 undergoes TIR 20. As shown in FIGS. 6(a) and 6(b), the light 2 enters a high index substrate 30 through an edge 28 via the coupling device 8. FIG. 6(a) is a face view of a face 26 of the high index substrate 30. FIG. 6(b) is an edge view of the high index substrate 30. Shown in FIGS. 7(a) and 7(b) are parasitic oscillations in a low index substrate 32. In FIGS. 7(a) and 7(b), the coupling device 8 introduces the light 2 into the low index substrate 32.

This present invention takes advantage of parasitic oscillations and uses them to increase the efficiency of contamination removal. With proper design, an electromagnetic beam or beams may be launched into a material such that the beam bounces around within the element via TIR and eventually strikes every area of the face. To support these parasitic oscillations, the edge of the material/substrate must be smoothed, for example by polishing, so as to be specularly reflective rather than diffusely reflective or scattering.

These parasitic oscillations offer two significant advantages. First, a laser beam, even a weak one, could be launched into the optical element as a probe. If there is no surface contamination, the beam continues to experience TIR (100% reflection). After suitably traversing a long path through the element, the beam could be detected. Any drop in laser power would indicate the presence (somewhere) of surface contamination. Second, a powerful laser beam would then be launched on the same or a similar parasitic oscillation path. This beam will also encounter the contaminated portion of the surface, but this more powerful beam will heat and remove the contamination via ATIR. Thanks to parasitic oscillations, this powerful laser beam seeks out the contamination at the speed of light and does not waste any of its power until it finds the contamination. This provides the present invention with a significant efficiency advantage compared to simple external illumination of the surface.

With conventional external illumination to clean surfaces, much of the laser power is wasted. This waste includes any light reflected by the contamination and any light that misses the contamination. In many practical cases, less than 1% of the surface is contaminated. Any laser beam that externally scans or illuminates the whole surface will then be at least 99% wasted.

In $CaF_2$ and other substrates with a refractive index below $\sqrt{2}$ (square root of two), planar parasitic oscillations will not naturally occur because the required angle of incidence on the face is greater than 45°, which means it will be less than 45° on the edge (where it will not experience TIR). There are two solutions to this situation. One is to render the edges highly reflecting by applying a dielectric or metallic thin film coating. A second solution is to use only parasitic oscillation paths involving "skew" rays (FIG. 7) which always strike the edge and face at greater than the critical angle.

It is important to note that no transparent coating will eliminate or change the existence of TIR. Any ray that would experience TIR without a coating will also experience TIR with a coating. However, the TIR may be moved from 34 at a substrate 39/air surface in FIG. 8(*a*) to 36 at a coating 37/air surface in FIG. 8(*b*) and the angle of incidence will be changed. This change in the angle of incidence allows the use of coatings to enhance the removal of contamination via ATIR. Such a coating may have mechanical advantages in addition to any optical (ATIR) advantages. For example, the coating may be harder or more scratch resistant than the substrate.

Figure 8A:
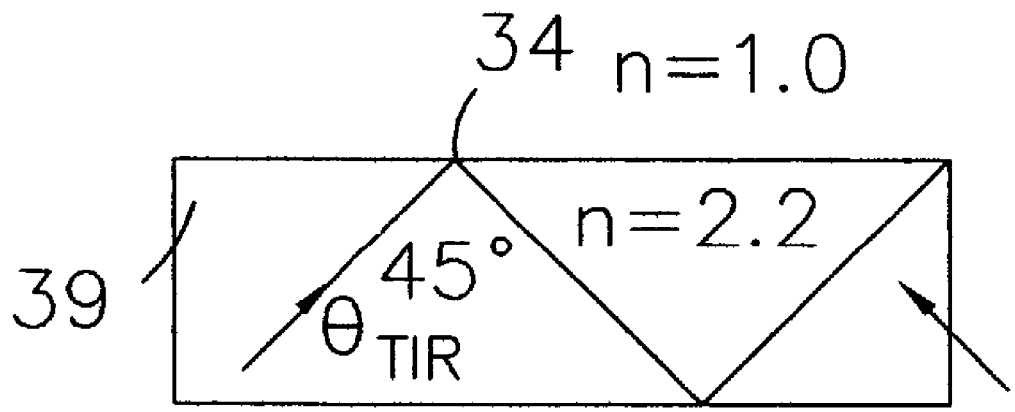
FIG. 8 shows an example of the effect of a coating on the surface of the substrate on total internal reflection.
Figure 8B:
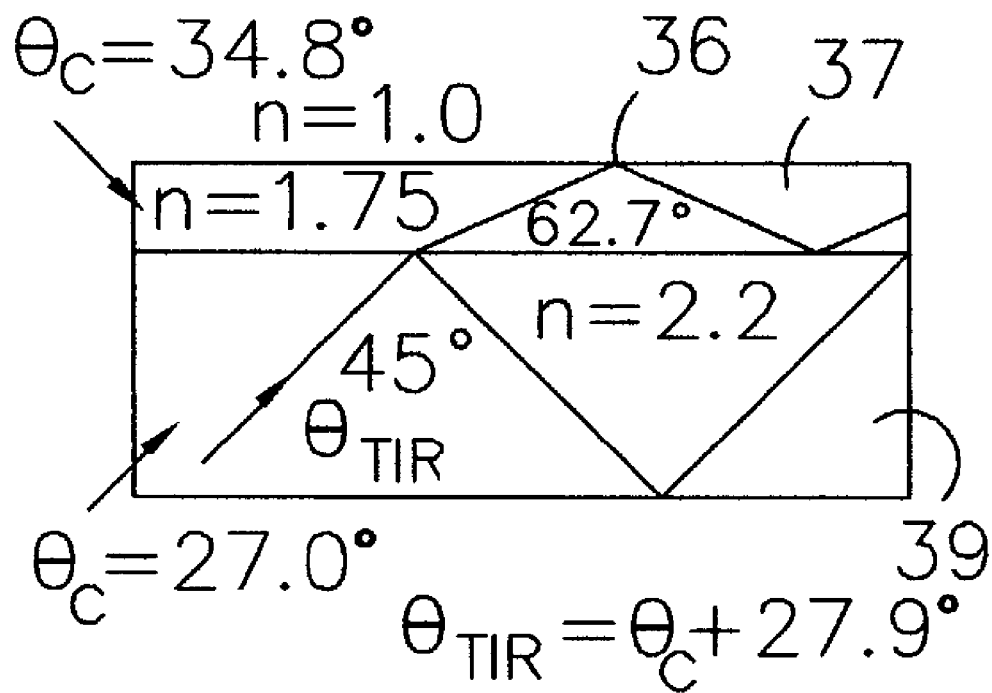

Even with high index substrates that readily support parasitic oscillations, a thin film coating on the face may enhance contamination removal by altering the angle of incidence for the internal reflection. As shown in FIG. 5, the absorption is dependent on the angle of incidence and the angle of incidence can be altered by a thin film coating (FIG. 8).

Whenever water is one of the contaminants of interest, the use of 2.94 μm light from an erbium laser is especially effective. Water has very strong (k'~0.28) absorption at this wavelength and solid-state erbium lasers are a mature technology. Water also has substantial absorption coefficients for wavelengths less than 0.2 μm and greater than ~1 μm.

Erbium lasers are widely available from manufacturers. Erbium lasers are preferred since they emit electromagnetic radiation at a wavelength that is strongly absorbed by water. Wavelengths in the 2.7 to 3.1 micrometer range are acceptable, but 2.94 micrometer is at or very near the peak of water's absorption and is readily available from erbium lasers. One common type of solid-state erbium laser emits pulses at a rate of 1 to 20 pulses per second. Each pulse is typically several hundred microseconds in duration and contains up to a few Joules of energy per pulse. Other versions of erbium lasers include a Q-switched version that emit pulses that are shorter (typically 5 to 200 nanoseconds) and contain slightly less energy per pulse. Mode-locked lasers emit even shorter pulses (typically 10 to 500 picoseconds) of appreciably lower energy at repetition rates than may be as high as millions per second. Other lasers emit femtosecond pulses, again at repetition rates up to millions per second. The average power of the most common erbium lasers is less than 20 Watts, but additional lasers or laser amplifiers can increase the power.

Continuous Emission (CW) or long pulse (typically 300 μs) light may be preferred for removing water, ice or absorbing film contamination. In aircraft applications, aerodynamic forces generally keep any water contamination to a thin layer. Shorter, Q-switched, or mode-locked pulses are generally better for removing particles. Experience indicates that absorbing particles are removed by the sudden thermal expansion caused by the laser heating. Many metals have very large (k'>1) absorption coefficients and lasers have been successfully used to remove metal particles from the polished surfaces of transparent substrates. Nonabsorbent particles may be removed due to forces from the electromagnetic field gradients resulting from attenuated or altered TIR.

An important application of the method and apparatus of the present invention is for the cleaning of semiconductor wafers. As microelectronic manufacturers push towards smaller and smaller integrated circuits, they become more and more concerned with removing smaller and smaller particles and contaminants from the surfaces of semiconductor materials. Most of the semiconductor materials are transparent at 2.94 micrometers and many experts feel that "capillary condensation" is the dominant force that holds very small particles to a surface. The present invention is expected to be especially effective at removing those particles, because the laser can be directly absorbed by the condensation and thereby blast the water and any particle above the water off of the surface.

Other applications of the method and apparatus of the present invention include the cleaning of "optical elements," which are especially sensitive to being clean. These optical elements include: any optical element, such as windows or nonmetallic mirrors, that transmit or reflect a high power laser beam (contamination is heated by the laser beam and damages the surface); any optical element, such as a lens or a (nonmetallic) mirror, in high precision optical instruments that are adversely affected by the scattered light from contaminants (microlithography, satellite photography, astronomical photography); and any optical element that is to be "optically contacted," as any contamination destroys the required material-to-material contact that leads to a welding together of the two substrates.

The laser beam or electromagnetic radiation may be introduced into the substrate by the coupling device 8 through the edge 28 or the side of the substrate as shown in FIGS. 6 and 7 or through an edge 6 as shown in FIG. 1. Coupling devices include coupling prisms and similar devices that will direct electromagnetic radiation into a substrate. If the edge is plane, the coupling prism may be a Porro or right angle prism. If the edge is a right circular cylinder, the hypotenuse face of the prism must be curved to match the edge of the substrate. Refractive index matching couplants (liquids or gels) may be used to contact the coupling prism to the substrate such that little if any light is reflected at the interfaces.

The methods and apparatuses of the present invention will be useful in cleaning multiple surfaces of a substrate. When a laser beam passes through a window, the first surface experiences external reflection and the second surface experiences internal reflection. The laser damage is not symmetric between the two surfaces. Because of phase changes, the oscillating electric field is stronger on the exit surface than it is on the entrance surface. At non-normal angles of incidence, calculating the ratio of electric field strengths becomes more complicated, but it is reasonable to expect that internal illumination will be more effective than external illumination at removing contamination. The present innovation will, in any case, have equal efficacy at cleaning both surfaces, since both surfaces experience total internal reflection.

The present inventors do no intend to be bound by any particular explanation of how altered total internal reflection may be used to clean contaminants from the surface of a substrate, however the explanations provided herein may provide an explanation for the physical mechanisms by which the removal of contaminants from the surface of the substrate is accomplished using altered total internal reflection. As is evident from the foregoing description, certain aspects of the present invention are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present invention.

What is claimed is:

1. A method of removing a contaminant from a surface of a material, the method comprising:
   directing electromagnetic radiation into the material,
   reflecting the electromagnetic radiation internally in the material at an angle of incidence equal to or greater than a critical angle so the electromagnetic radiation undergoes total internal reflection,
   transmitting, via altered total internal reflection, a portion of the electromagnetic radiation through the surface of the material, and
   removing the contaminant from the surface of the material via the coupling of the transmitted portion of electromagnetic radiation into the contaminant.

2. The method according to claim 1, wherein an edge of the material or a surface of the material is polished to provide for specular total internal reflection or parasitic oscillations of the electromagnetic energy.

3. The method according to claim 1, wherein the material comprises at least one coating on at least one edge of the material, on at least one surface of the material, or on a combination thereof.

4. The method according to claim 1, wherein an edge or a surface of the material has increased reflectiveness to the internally reflected electromagnetic radiation by the addition of at least one coating.

5. The method according to claim 1, further comprising mating a device to a side surface of the material which enhances introducing the electromagnetic radiation into the material and internally reflecting the electromagnetic radiation in the material to clean a planar surface of the material.

6. The method according to claim 1, further comprising at least one additional cleaning technique.

7. The method according to claim 6, wherein the additional cleaning technique comprises flowing gas across the surface to be cleaned to minimize redeposition of contaminants or applying ultrasonic energy to the surface to be cleaned.

8. The method according to claim 1, further comprising applying an additional substance to the surface to enhance the removal of the contaminant by the internally reflected electromagnetic radiation.

9. The method according to claim 8, wherein the additional substance absorbs the electromagnetic radiation.

10. The method according to claim 8, wherein the additional substance reduces adhesion or stickiness of the contaminant to the surface of the material.

11. The method according to claim 8, wherein the additional substance reduces the likelihood that the removed contaminant will reattach itself to the surface of the material.

12. The method according to claim 8, wherein the additional substance mixes with or attaches itself to the contaminant.

13. The method according to claim 1, further comprising selecting a wavelength of electromagnetic radiation that is absorbed by the contaminant, by an added substance to the surface, or by both the contaminant and the added substance to the surface.

14. The method according to claim 1, further comprising directing more than one wavelength of electromagnetic radiation into a side surface of the material and reflecting more than one wavelength of electromagnetic radiation internally in the material to remove a contaminant from a planar surface of the material.

15. The method according to claim 1, wherein the electromagnetic radiation is infrared, visible, ultraviolet, or mixtures thereof.

16. The method according to claim 1, wherein the electromagnetic radiation is from a laser.

17. The method according to claim 16, wherein the laser is a continuous emission, Q-switched, mode-locked or femtosecond laser.

18. The method according to claim 16, wherein the laser emits light with a wavelength of between about 2.5 to about 3.2 micrometer.

19. The method according to claim 18, wherein the laser is an erbium laser.

20. The method according to claim 16, wherein the laser is a neodymium, chromium, excimer, carbon dioxide, erbium, semiconductor laser, or optical parametric amplifier.

21. The method according to claim 1, wherein a source of the electromagnetic radiation is at least one light emitting diode.

22. The method according to claim 1, wherein a source of the electromagnetic radiation is pulsed.

23. The method according to claim 1, wherein a source of the electromagnetic radiation is nominally continuous.

24. The method according to claim 1, wherein the electromagnetic radiation is from more than one source.

25. The method according to claim 1, wherein the electromagnetic radiation is from a halogen or an infrared lamp.

26. The method according to claim 1, wherein the material is a semiconductor.

27. The method according to claim 1, wherein the material is a mirror, view port, window, laser window, or architectural window.

28. The method according to claim 1, wherein the surface is the outer surface or window of a light, automobile headlight, or searchlight.

29. The method according to claim 1, wherein a cleanliness of the surface is measured by detecting an amount of altered total internal reflected electromagnetic radiation leaked outside of the material.

30. The method according to claim 1, wherein the same electromagnetic radiation measures the level of cleanliness of the surface and removes the contaminant from the surface.

31. The method according to claim 1, further comprising:
   detecting the contaminant on the surface with a first amount of electromagnetic radiation, and
   removing the contaminant on the surface with a second amount of electromagnetic radiation.

32. The method according to claim 1, wherein the material has a planar surface and a side surface, wherein a source of electromagnetic radiation is directed into the side surface of the material to remove a contaminant from the planar surface of the material.

33. The method according to claim 1, wherein the contaminant is a phase of water.

* * * * *